(12) United States Patent
Spahn

(10) Patent No.: US 7,073,939 B2
(45) Date of Patent: Jul. 11, 2006

(54) METHOD AND SYSTEM FOR GENERATING AN X-RAY EXPOSURE

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/815,040

(22) Filed: Mar. 31, 2004

(65) Prior Publication Data

US 2004/0240609 A1   Dec. 2, 2004

(30) Foreign Application Priority Data

Mar. 31, 2003   (DE) ................. 103 14 536

(51) Int. Cl.
*H05G 1/02* (2006.01)
(52) U.S. Cl. .................. 378/196; 378/197; 378/189
(58) Field of Classification Search ............. 378/62, 378/63, 68, 4, 19, 39, 25, 196, 197
See application file for complete search history.

(56) References Cited

U.S. PATENT DOCUMENTS

| 4,807,273 A | * | 2/1989 | Haendle | 378/197 |
| 4,894,855 A | * | 1/1990 | Kresse | 378/196 |
| 6,200,024 B1 | * | 3/2001 | Negrelli | 378/197 |
| 2002/0054662 A1 | * | 5/2002 | Verdonck et al. | 378/62 |

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

In a method and system for generating an x-ray exposure of an examination subject extending in a longitudinal direction and exhibiting, in a main projection direction, a geometry that is curved at least in sections, an x-ray source and an x-ray detector are respectively positioned and aligned appropriately with regard to one another and to the section to be acquired of the exposure subject in order to generate partial exposures along a curved course substantially adapted to the geometry of the exposure subject. The partial exposures of the sections subsequently are combined into an overall x-ray exposure of the exposure subject.

25 Claims, 4 Drawing Sheets

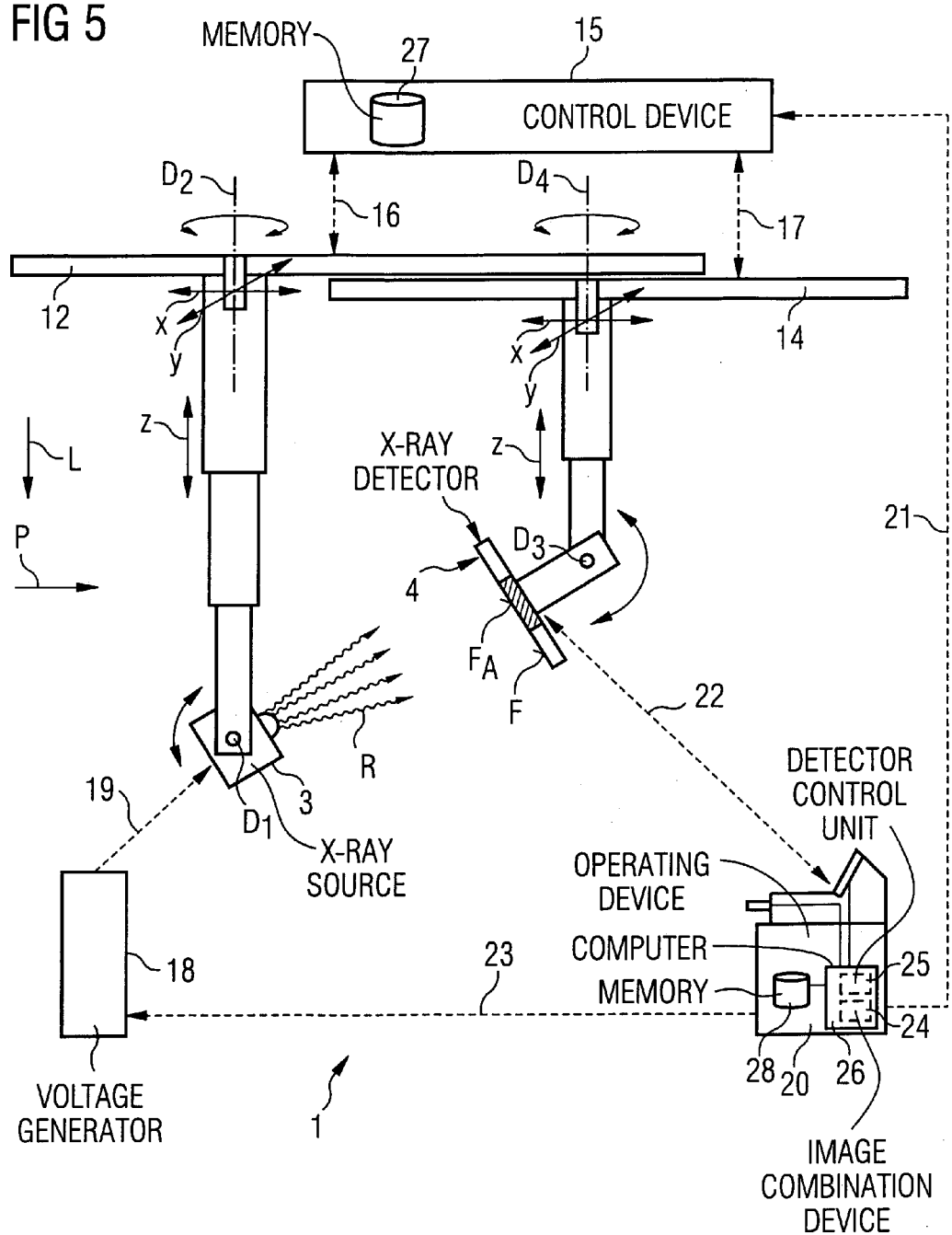

METHOD AND SYSTEM FOR GENERATING AN X-RAY EXPOSURE

BACKGROUND OF THE INVENTION

1. Field of the Invention

The present invention concerns a method and system for generating an x-ray exposure of an examination subject exhibiting a curved geometry.

2. Description of the Prior Art

Methods are known for generating an x-ray exposure of an exposure subject extending in a longitudinal direction which, at least in sections, exhibits a curved geometry in a main projection direction transverse to the longitudinal direction, wherein initially partial exposures of individual sections of the exposure subject are generated by positioning of an x-ray source and an x-ray detector at various positions along the longitudinal direction of the exposure subject, and then the partial exposures of the sections are combined into an overall x-ray exposure of the exposure subject. Moreover, x-ray systems are known for generating an x-ray exposure of such an exposure subject; which have an x-ray source and an x-ray detector that can each be moved at least along the longitudinal direction of the exposure subject; under the control of a control device, to generate partial exposures correlated to individual sections of the exposure subject; and having an image combination device that forms an overall x-ray exposure of the exposure subject from the partial exposures, and/or with means to identify the partial exposures for a later combination.

Digital x-ray detectors have been changing classical radiography for years. Among the newer technologies that have been in use or are just about to come to market are image intensifier camera systems based on television or CCD cameras, storage film systems with integrated or external reader unit, systems with optical coupling of the converter film to CCDs or CMOS chips, selenium-based detectors with electrostatic readout and solid-state detectors with active readout matrices. Common to all of these technologies is that the x-ray information ultimately exists digitally both as to position, in the form of a two-dimensional pixel structure, and in the signal amplitude in the form of grey scale values with given bit depths.

Such digital x-ray systems enable a series of new applications such as, for example, the representation of organs that are very much larger than the size of the detector surface of the detector that is used. In classical radiography, such exposures are made with the aid of oversize x-ray films at a larger distance of the exposure subject from the x-ray radiator. In contrast to this, with digital detector systems, it is possible to acquire an exposure series in the above-specified manner with individual partial exposures of the examination subject, and subsequently to combine the individual images with an image fusion method, so that a large overall exposure results, A greater flexibility is achieved with such digital methods, and a better image quality is achieved than with classical method.

To generate an exposure series, the x-ray source (also called x-ray radiator in the following) and the x-ray detector matched thereto are shifted in a straight line along the longitudinal direction of the exposure subject, and thereby produce partial exposures at specific positions. Normally, care is taken that the individual exposures of adjacent partial sections respectively overlap somewhat at their ends. This simplifies the precise positioning of the individual partial exposures relative to one another for the combination of the individual partial exposures into the desired overall x-ray exposure of the examination subject. Examples of such examinations in which larger exposure subjects (normally extending in a longitudinal direction) are acquired by a number of partial exposures, and from this an overall exposure is formed, are whole-body exposures or exposures of arms, legs, vessels or the spinal column of a patient. It is always important in such x-ray exposures that the exposed subject be correctly imaged as precisely as possible with regard to his individual structures. This is particularly a problem given complicated skeletal structures such as the spinal column. In the case of a spinal column exam, in addition to the shape, in particular the structure at the edge of the vertebral body and the intervening space between the individual vertebrae, meaning the representation of the intervertabral discs, are of significant importance. With the known type of generation of the individual partial exposures by means of an x-ray source moving in a straight line and an x-ray detector running in parallel, shadow formations are disadvantageously created directly in the edge regions and the intervening spaces between the vertebrae due to overlapping of adjoining vertebrae and due to parallax effects. This can lead to defects that are not clearly associated with a specific vertebra. A precise association of the defects with a specific vertebrae or with specific vertebrae is, however, indispensable for therapy. This means the overall x-ray exposure of a spinal column generated with a known digital acquisition method normally exhibits the same shadow formation of the individual vertebrae at the edge regions as is also the case given the classical acquisition method, in which the entire spinal column is recorded on an oversize x-ray film. A similar problem is represented by exposures of other large skeletal structures, in particular in the joint areas.

SUMMARY OF THE INVENTION

An object of the present invention to improve the x-ray acquisition methods and x-ray systems of the above-cited type, so that a better qualitative representation is achieved, even for an exposure of a subject with a complex geometry, in particular an exposure of a spinal column.

This object is achieved by an x-ray acquisition method according to the invention wherein an x-ray source and are x-ray detector to generate partial exposures, with the x-ray source and the x-ray detector being respectively matched to one another with regard to their radiation or acquisition direction and to the section to be acquired of the exposure subject, and wherein the x-ray source and the x-ray detector are positioned and aligned along a curved course essentially adapted to the geometry of the exposure subject—meaning essentially following the geometry of the exposure subject. For this, the inventive x-ray system has a control device for appropriately positioning and aligning the x-ray source and the x-ray detector to generate such partial exposures along the desired curved course.

Thus, to generate the partial exposures, the x-ray source and the x-ray detector are not simply shifted parallel to one another linearly along the longitudinal direction of the exposure subject, and consequently not only simple partial projections of the individual sections are produced in the main projection direction standing perpendicular to the longitudinal direction of the exposure subject. The overlappings and parallax effects due in particular to the curved geometry, and the shadow formations caused thereby, can be reduced or even completely prevented. The quality of the overall exposure thus can be significantly improved in a simple manner. Given use of such a method to acquire a spinal column, the structures at the vertebrae ends and between the individual vertebrae are also well represented in detail.

To adapt to the curve of the exposure subject, the x-ray source and the x-ray detector preferably are each positioned and aligned relative to one another and to the section to be acquired of the exposure subject, such that the current projection direction given the appertaining partial exposure (also called "partial exposure projection direction" in the following) lies essentially at a right angle to the section to be acquired of the exposure subject, meaning that the partial exposure projection direction is at a right angle to the local extension direction of the appertaining section or, respectively, given significantly curved sections, for example, at a right angle to a median (middle or average) tangent or the like, Undesired superimposition and parallax effects in the respective partial exposure due to a non-alignment of the exposure subject section with regard to the projection direction are almost completely prevented. In the acquisition of a spinal column image, it is thus ensured that, even in the curved regions of the spinal column, adjacent vertebrae ends do not overlap in the current partial exposure projection, and thus the details of the vertebrae ends and the intervertabral disk structures lying between them are acquired with much more detail being visible than was conventionally possible.

The current partial exposure projection direction is determined by the positions of x-ray source and x-ray detector and their alignment with regard to the subject. The x-ray source and the x-ray detector of the x-ray system preferably are pivotable around an axis perpendicular to the longitudinal direction of the exposure subject and perpendicular to the main projection direction.

Moreover, one or both of the x-ray source and the x-ray detector is/are positioned on a curve essentially following the geometry of the exposure subject. The source is positioned on a curve preceding (with respect to radiation propagation) the subject, and the detector is disposed on a curve after the subject. This means the x-ray source and/or the x-ray detector are not moved, is conventional, as along a straight line parallel to the longitudinal direction of the exposure subject, but rather are moved along a curve that is adapted to the geometry of the exposure subject. For the acquisition of a spinal column image series, the positioning of the x-ray source and/or of the x-ray detector ensues, for example, along a double-s curve. This allows, in each partial exposure, independent of the current partial exposure projection direction, the x-ray source and the x-ray detector to have approximately the same separation from one another and from the currently exposed section of the exposure subject.

To accomplish this, the x-ray source and/or the x-ray detector must additionally be movable at least in the primary projection direction. The x-ray source and/or the x-ray detector preferably are positioned with suitable degrees of freedom, such that each or both can respectively be positioned on an arbitrary, nearly freely selectable curve. For example, both the x-ray source and the x-ray detector can be freely positioned and pivoted in all three spatial directions, and thus can move automatically Siong arbitrary curves in space using corresponding actuators operated by of a control device, and this can be pivoted in arbitrary directions. In this case, only the control device must be correspondingly programmed, so that the x-ray source and the x-ray detector are moved along the desired curves in the generation of the partial exposures of the individual sections of the examination subject, and by pivoting an alignment of both components ensues such that the current partial exposure projection direction is optimally perpendicular to the section to be acquired of the exposure subject.

In a preferred exemplary embodiment to generate the exposure series, an x-ray detector is used which has a relatively narrow active detector surface in the longitudinal direction of the exposure subject. With such a narrow detector surface a larger number of partial exposures must be produced in order to generate an overall x-ray exposure, but the advantage of a higher number of partial exposures is that a significantly better adaptation of the projection geometry of the exposure series to the geometry of the exposure subject is possible, and distortion artifacts can be minimized. By the use of a detector that is narrow in the longitudinal direction of the exposure subject, it is ensured that, given the increased number of partial exposures, the overlap between the individual adjacent partial exposures is only as large as is necessary for a later merging of the individual partial exposures, and unnecessary regions are not doubly acquired. Achieving this with the conventional use of digital detectors would be associated with significant loss of time for the readout of the unnecessary detector regions. The shortened readout process achieved with the inventive method and system enables a faster image series production and therefore provides for a reduction of the movement artifacts and distortion artifacts.

In an alternative preferred exemplary embodiment, only one narrow region of a detector surface of an x-ray detector in the longitudinal direction of the exposure subject is used as the active surface, This has the advantage that a "normal" digital x-ray detector with the typical dimensions can be used. The inventive x-ray system thus also can be used without retrofitting for different applications. For use of the system for implementing the inventive method, it is provided with a suitable detector control so that only a smaller detector surface is activated or read out, so the same timesavings per exposure is achieved as is the case with use of a narrower detector. The middle region of the detector surface is preferably used as he active surface.

In order to determine the curves along which the x-ray source and the x-ray detector must be moved and the individual positions on the curves at which both components must be respectively appropriately positioned and aligned in order to generate the individual partial exposures, there are various possibilities:

For example, for each possible exposure subject a curve set can be predetermined and stored in a suitable memory of the control device. Such a curve set should include all data about the position and alignment of the x-ray source and the x-ray detector for the individual partial exposures. This means a curve set includes, for example, a curve course for the x-ray source and a curve course for the x-ray detector, and additionally the exposure positions along each curve and the alignment at the individual positions. Alternatively, it is possible to store a formula with which the curve set is analytically calculated.

Normally, it is not assumed that various similar exposure subjects exhibit the same size. For example, the length of a spinal column is associated with the total body size of the examination subject.

In order to select the correct curve set for each individual examination, another possibility for a standard curve set to be predetermined for an exposure subject type, for example a normally shaped spinal column, and this standard curve set is appropriately scaled corresponding for imaging the current exposure subject. Alternatively, various curve sets for exposure subjects with different dimensions can be predetermined for an exposure subject type. The individual exposure subject types, in this concrete example, can be various types of spinal columns that are differently shaped, for example a normally-shaped spinal column as well as spinal columns with typical, frequently occurring lordosis abnormalities.

The anticipated length of a spinal column of an examination subject can be determined, for example, on the basis of the external body dimensions of the subject. This can ensue automatically by, for example, the x-ray radiator first being moved to precisely defined points at different heights of the subject, and these heights are then manually or automatically stored by the system. With such a data set, the control device can itself appropriately scale a predetermined standard curve set, or select the best curve set from a number of predetermined curve sets.

In another preferred variant, for more precise determination of the geometry and/or the dimension of the examination subject, and thus to determine an appropriate curve set beforehand, a reference x-ray exposure (also called a localizer or topograph) is made in a plane lying substantially parallel to the longitudinal direction of the examination subject and substantially parallel to the main projection direction. For the examination of a spinal column, a lateral whole-body exposure of the subject can first be generated, preferably with only a low x-ray dose. Alternatively, reference exposures already generated on other apparatuses, for example other x-ray apparatuses, computed tomography systems or magnetic resonance tomography systems can also be used.

The inventive method is suitable, as discussed, particularly for spinal column exposures in humans or animals. It is also suitable for exposures of other subjects which extend, at least in one longitudinal direction, beyond the dimensions of a typical digital x-ray detector, and which exhibit a curved geometry.

The inventive method and system also can be used for exposure subjects having such a large extent in two directions. For this purpose, partial exposures which form an "exposure line (or "exposure row" ) are first produced in a first longitudinal direction, and a second exposure series with partial exposures in an adjacent second "exposure line" are generated with a specific displacement (offset) in a direction perpendicular to this first longitudinal direction, and so on. In this manner, matrix-like individual sections of the exposure subject extending two-dimensionally are acquired that are then combined into an overall exposure. An inventive adaptation to the geometry of the examination subject thus is possible in each of the two main directions.

DESCRIPTION OF THE DRAWINGS

FIG. 5 is a schematic illustration of an exemplary embodiment of an inventive x-ray system.

DESCRIPTION OF THE PREFERRED EMBODIMENTS

In the figures and the further explanations, it is assumed that an optimally shadow-free representation of the spinal column of a person is generated by means of the inventive method. As previously explained, however, the invention is not limited to such an application.

Figure 1:
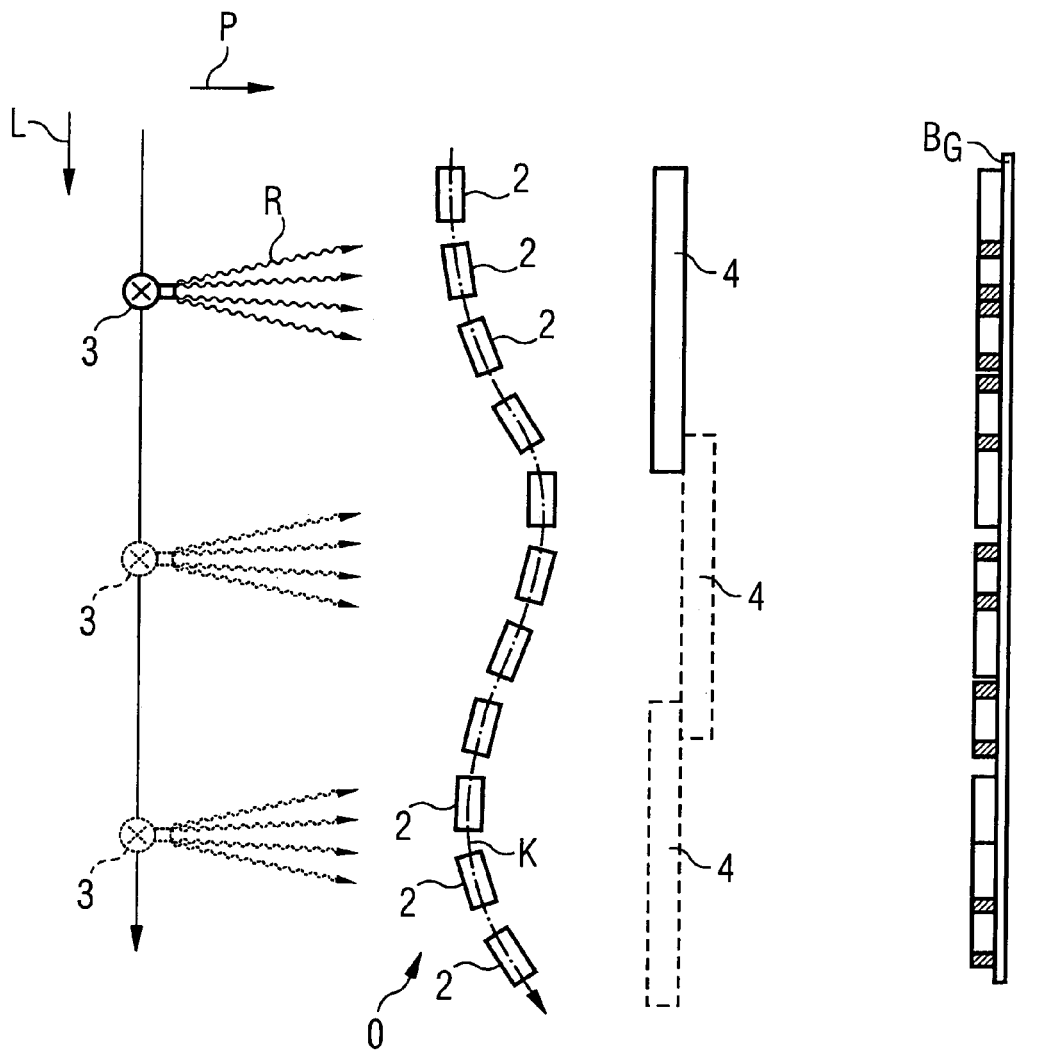
FIG. 1 illustrates the basic procedure for acquiring a spinal column image according to the prior art.

FIG. 1 schematically shows as an exposure subject, the individual vertebras 2 of a spinal column O in a typical "double-s shape". This spinal column O essentially extends in a longitudinal direction L.

Conventionally, a complete exposure of such a spinal column O is generated by an x-ray source 3 and an x-ray detector 4 being moved in tandem in front of and behind the spinal column O on straight lines parallel to the longitudinal direction L. At specific positions—here at three positions—partial exposures of adjacent sections of the spinal column O are generated. These partial exposures are then combined into an overall x-ray exposure $B_G$. A problem with this acquisition method is that, due to the typical double-s shape, the spinal column O exhibits a geometry (curve K) that is curved in the projection direction P that here is at a right angle to the longitudinal direction L. Parallax effects and superimpositions of individual vertebrae are thereby created, such that shadow formations occur in the overall x-ray exposures $B^G$. These shadows in particular prevent the end regions of the vertebrae 2 (that are in most cases clinically very important) and intervening spaces between the vertebrae 2, the intervertabral discs, from being correctly recognizable on the exposure.

Figure 2:
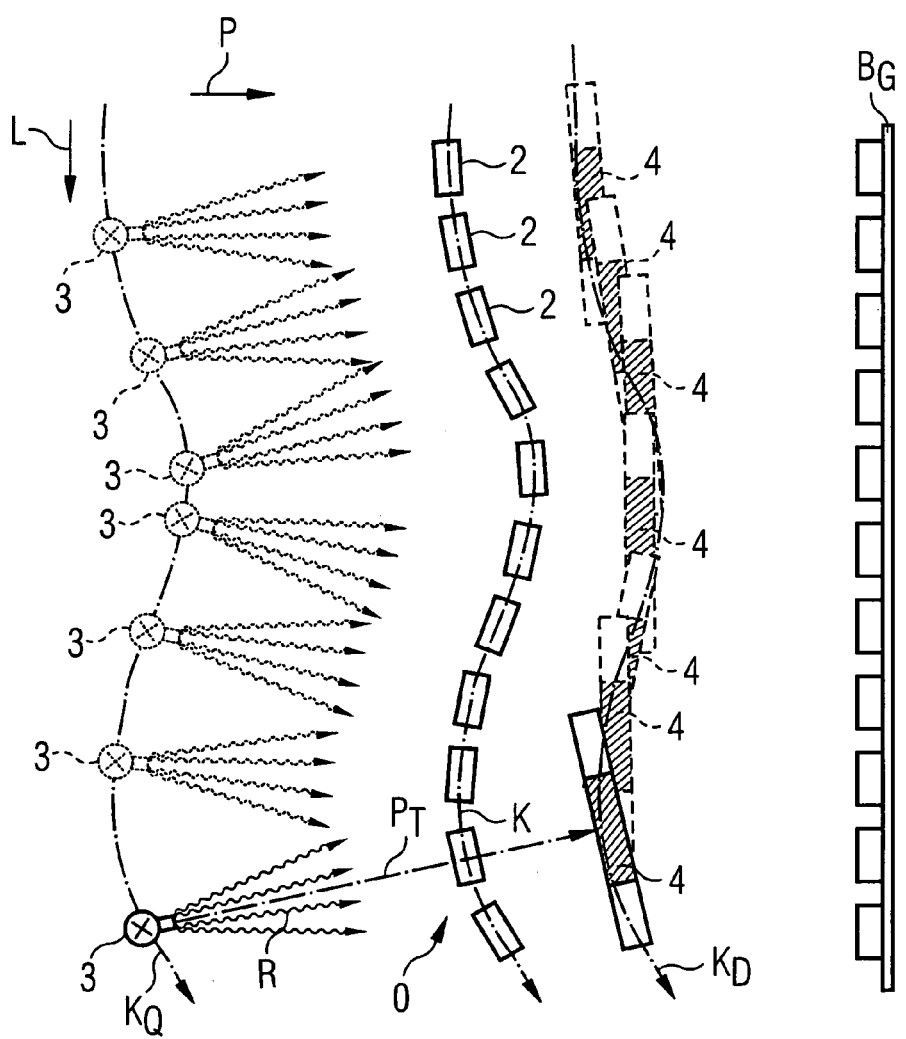
FIG. 2 illustrates the basic procedure of the inventive method for acquiring a spinal column.

In order to prevent this, in the inventive method according to FIG. 2 both the x-ray radiator 3 and the x-ray detector 4 are moved along curves $K_Q$, $K_D$ that are adapted to the geometry of the spinal column O, meaning they essentially follow the curve K of the spinal column O. At each exposure position $S_1$, $S_2$ through $S_N$, the x-ray radiator 3 and the x-ray detector 4 are appropriately aligned to one another such that the current partial exposure projection direction $P_T$ for that partial exposure is optimally perpendicular to the acquired section of the spinal column, as is shown at the bottom in FIG. 2. The parallax effects and superimpositions of the individual vertebrae in the end regions thereby are prevented already in the partial exposures, so that consequently these effects cannot influence the combined exposure $B_G$.

In order to achieve an optimally good adaptation of the individual partial exposures to the curve K of the spinal column O, significantly more partial exposures are produced at different positions than is the case according to the prior art. In the exemplary embodiment according to FIG. 1, only three partial exposures were produced, and in the inventive exemplary embodiment according to FIG. 2 in total seven individual partial exposures were produced. The number of partial exposures can in principle be arbitrarily selected.

In order to enable such a number of partial exposures from different positions to be produced in a reasonable time, in the shown exemplary embodiment only the middle partial region of the detector 4 is used as an active surface $F_A$. This means, for example given a typical square detector of 40×40 cm², only the central region of 40×20 cm² is used, whereby the 20 cm extent runs in the longitudinal direction L of the spinal column O. The increase of the number of partial exposures with a simultaneous reduction of the detector surface results in the distortion artifacts being minimized and the projection geometry being optimized.

Figure 3:
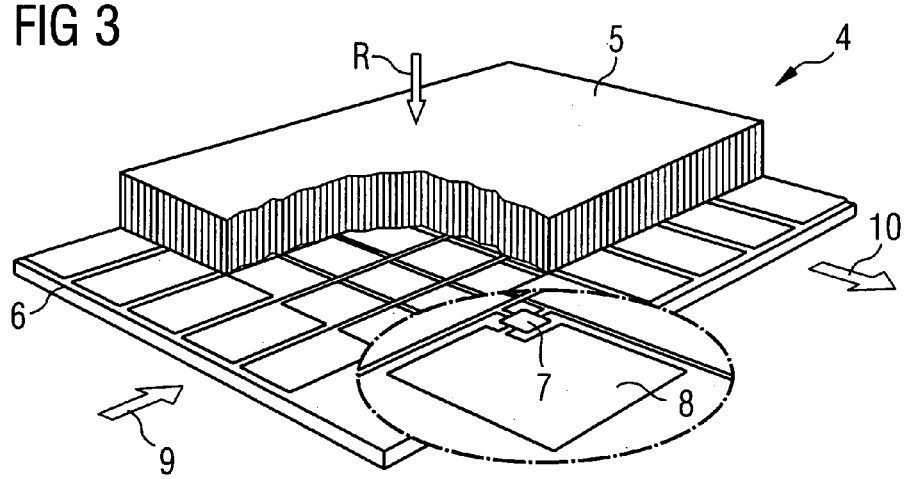
FIG. 3 is a perspective view, partly in section, of a digital x-ray detector with an active matrix, with an enlarged illustration of a photodiode matrix element with an associated switching element, suitable for use in the inventive method and system.

For further explanation, reference is made to FIG. 3, which shows the assembly of a typical solid-state x-ray detector 4. Such an x-ray detector 4, in the uppermost position in the x-ray beam propagation direction R, an x-ray conversion layer 5, for example made from cesium iodide or a similar material, In this x-ray conversion layer 5, the incoming x-ray radiation is converted into light. This light is then detected and transduced into electrical charge by an active readout matrix 6—the actual image sensor 6—located directly behind the based on amorphous silicon or something similar. For this, the matrix 6 has a number of photodiode elements 8 that can be read out individually via an active circuit element 7, for example an integrated transistor or a diode. The control ensues, for example, via a line driver 9 that is represented here by the arrow. The readout ensues column-by-column in the arrow direction 10. The emitted signals are suitably amplified, multiplexed and supplied to ADCs. The detector 4 is a typical solid-state detector assembly, such that the details with regard to the assembly and the control and the readout thereof are known to those skilled in the art and do not have to be explained further.

With suitable control of the line driver, it is possible without anything further to read out only the middle column of the detector 4, meaning to actually use only the middle region of the detector 4. The readout process is thereby correspondingly shortened, such that a significantly faster image series is possible in relation to the method shown in FIG. 1, in which the entire surface of the detector 4 is used. The probability of the occurrence of movement artifacts or distortion artifacts thus is reduced. The faster production of the image series compensates for the fact that a higher number of partial exposures are produced in the inventive method, such that overall the exposure according to the inventive method generally is only insubstantially longer than a spinal column exposure according to the known method.

Figure 4:
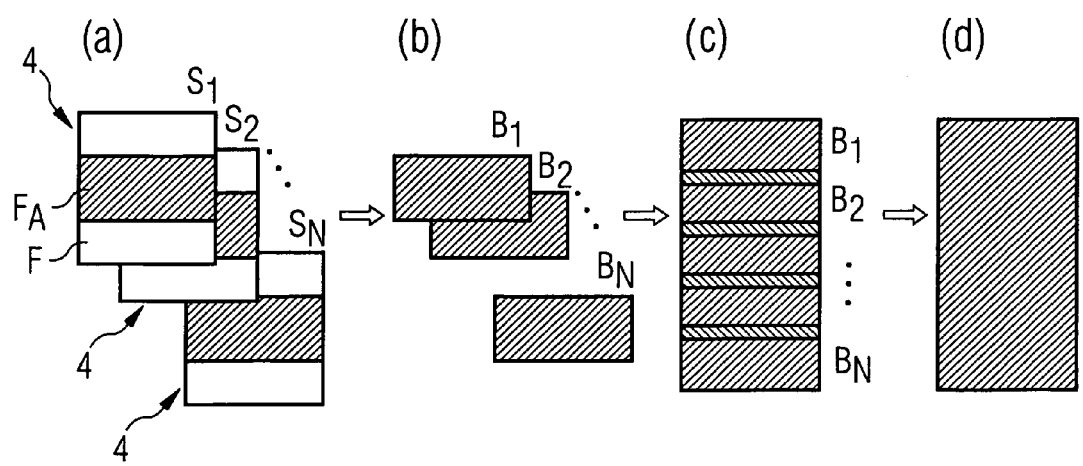
FIG. 4 schematically illustrates a procedure in accordance with the inventive method for producing an overall x-ray exposure from the individual partial exposures.

FIG. 4 schematically shows again the method to assemble the overall x-ray exposure $B_G$ from the individual partial exposures $B_1$, $B_2$ through $B_N$.

First, individual exposures are produced at various positions $S_1$, $S_2$ through $S_N$ along the longitudinal direction L of the spinal column O, as this is shown in step (a). In this case, only a middle strip of the total detector surface F of the x-ray detector 4 is ever used as an active surface $F_A$.

In the next step (b), the individual image contents that have been acquired by the active surface $F_A$ at the individual positions $S_1$, $S_2$ through $S_N$ (meaning the partial exposures $B_1$, $B_2$ through $B_N$) are read out. These are combined in the step (c) using a typical image fusion method known to those skilled in the art. By means of the overlap region between the successive individual exposures $B_1$, $B_2$ through $B_N$, these are matched and adapted in terms of grey values such that ultimately in the last step (d) the desired overall x-ray exposure $B_G$ is created.

An exemplary embodiment of an inventive x-ray system 1 is shown in FIG. 5.

The x-ray system 1 in FIG. 5 has an x-ray radiator 3 that is suspended such that it can be arbitrarily moved in all three spatial directions x, y, z. For this, the x-ray radiator 3 is suspended on a telescoping mount 11 on a ceiling rail 12. By extending the telescoping mount 11, the height of the x-ray radiator 3 can be set in the z-direction; by shifting the mount 11 on the suspension rail 12, or by shifting the suspension rail 12 in space, the x-ray radiator 3 can be positioned in the x-direction and the y-direction. Moreover, an axial rotation of the mount 11 together with the x-ray radiator 3 around the longitudinal axis $D_2$ of the mount 11 is possible. Furthermore, the x-ray radiator 3 can be arbitrarily pivoted around an axis $D_1$ perpendicular to the mount 11.

In the same manner, an x-ray detector 4—in the present case a solid-state detector 4 according to FIG. 3—is suspended on a telescoping mount 13 and a ceiling rail 14, such that it can likewise be moved freely in space with regard to height (z-direction) and in the x and y directions. This x-ray detector 4 also can be pivoted left and right around an axis $D_4$ in the longitudinal direction of the mount 13, as well as up and down around a second axis $D_3$ perpendicular to this first axis $D_4$.

The x-ray system 1 has suitable drives and actuators (not shown) with which the positioning of the x-ray radiator 3 and of the x-ray detector 4 can ensue fully automatically. For this purpose, the actuators are controlled by a control device 15 via control lines 16, 17.

The x-ray system moreover has a typical voltage generator 18 that supplies the x-ray source 3 with the necessary high voltage via a supply line 19. This supply typically ensues via the ceiling rail 12 and via the mount 11.

The entire system 1 is centrally controlled by an operating unit 20 that at the same time also forms the image station with a suitable monitor. The voltage generator 18 and the control device 15 to position the x-ray radiator 3 and the detector 4 are controlled by this operating unit 20 via control lines 23, 21. Moreover, the detector 4 is controlled or read out by the operating unit 20 via a control line 22 with a corresponding detector control unit 25. All control and supply lines 16, 17, 19, 21, 22, 23 are shown in FIG. 5 only schematically in the form of dashed arrows.

The read out images then can be evaluated in a typical image evaluation device (not shown) and shown on the monitor or (if—as in the present case—partial exposures of specific sections of an examination subject O are concerned) can first be combined into an overall exposure in an image combination device 24 which can also be part of the image evaluation device, The partial exposures and the overall exposure can be buffered or ultimately archived in a storage 28. The image combination device (which may be, a module of the image evaluation device) and the detector control device 25 can be installed on a central computer 26 of the operating unit 20 in the form of software modules.

The x-ray system 1 also can include all components typically found in conventional x-ray systems. For example, the operating unit 20 can have interfaces to connect to image information systems or management information systems in a clinic or doctors practice or the like. These extra components are not explicitly shown here for better clarity.

The system shown in FIG. 5 has the advantage that the x-ray source 3 and the x-ray detector 4 can execute nearly arbitrary curves in space due to the independent suspension on the movable and rotatable ceiling mounts 11, 13. By means of the control device 15, in the exposure series for the spinal column O both the x-ray radiator 3 and the x-ray detector 4 can be moved in curves $K_Q$, $K_D$ (see FIG. 2), each being is optimally well adapted to the anatomy of the spinal column O. By suitable pivoting around the suspension axis $D_1$, $D_3$, the x-ray radiator 3 and the x-ray detector 4 can be automatically aligned at each position, such that the current partial exposure projection direction $P_T$ is optimally perpendicular to the section to be acquired of the spinal column O. Shadow formations and superimpositions of the operator console thereby are largely minimized, as is shown in FIG. 2.

There are various possibilities to find the correct curves or image positions and alignments for the x-ray source 3 and the x-ray detector 4 for a particular use.

Various curve sets which take into account various body sizes, and thus various lengths of the spinal column O, can be stored in a memory 27 of the control device 15. Such a curve set includes a curve $K_Q$ for the x-ray radiator 3 and a curve $K_D$, appropriate to the curve $K_Q$ for the x-ray detector 4, as well as the positions at which the individual partial exposures exist and the alignments of the x-ray radiator 3 and the x-ray detector 4 at the respective position. The best-suited curve set is then determined by comparison of the actual body size of the patient and the stored set of curves of the system.

As an alternative, only a standard curve set that corresponds to a normal size of the spinal column is provided in the system. To adapt this normal curve set, given a stationary patient the x-ray radiator 3 is first moved to a well-defined point at the height of the head, for example to eye height. The height is then manually or automatically stored by the system. The x-ray radiator 3 is subsequently moved to a further well-defined point at the height of the pelvis, for example at the height of the pelvic bone. This height is also stored. A factor with which the curve set stored in the system can be scaled then results from the difference of the heights. For this, a fit method can be used. A simple multiplication with a factor F, which corresponds to the measured height divided by a normal height, is also possible.

The control system then automatically determines appropriate positions of the x-ray radiator 3 and the x-ray detector 4, in that the acquisition procedure is simulated, for example by computer. This ensures that the partial exposures generated in the various positions have a desirable overlap for the image fusion.

If the individual partial exposures are not already immediately merged in the image evaluation unit of the operating unit 20, it is possible to store the individual partial exposures with suitable identifiers, such that they can be arbitrarily combined without anything further at a later point in time on another computer.

It should once again be noted out that the specific method procedures or details of the x-ray system 1 shown in the figures are only exemplary embodiments. Many variations of the exemplary embodiments are possible without departing from the framework of the invention. In particular, it is possible for the control device 15 and/or the memory 27 in which the curve sets are stored to be integral components of the operating unit 20. Likewise, functions of the operating unit 20 can be sourced out or distributed on a network of different servers that functionally cooperate.

The inventive method and system are suitable for retrofitting existing x-ray systems which already have a motorized x-ray source 3 and a corresponding x-ray detector 4 that can be moved into arbitrary positions, by providing an inventive control device 15 and a suitable detector control device in order to use these systems according to the inventive method. If such a system already has a control device with suitable processors, an update of the control software with suitable control software modules may be sufficient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating an x-ray exposure of an examination subject having a longitudinal extent in a longitudinal direction and exhibiting a curved geometry throughout said longitudinal extent, in a projection direction perpendicular to said longitudinal direction, comprising the steps of:

disposing an x-ray source and an x-ray detector respectively at opposite sides of the examination subject;

moving said x-ray source and said x-ray detector in coordination with each other in said longitudinal direction along a curved path, substantially co-extensive with said longitudinal extent and substantially conforming to said curved geometry of said subject;

at each of a plurality of successive positions along said curved path, activating said x-ray source to generate a partial exposure of said subject, thereby obtaining a plurality of partial exposures; and combining said plurality of partial exposures to form an overall x-ray exposure of said curved geometry of said subject.

2. A method as claimed in claim 1 comprising, at each of said positions, aligning said x-ray source and said x-ray detector with each other and with respect to a portion of said subject to be acquired in the partial exposure at that position, for causing a projection direction associated with the partial exposure at that position to be substantially at a right angle relative to said portion.

3. A method as claimed in claim 1 comprising moving each of said x-ray source and said x-ray detector along respective curves corresponding to said curved geometry.

4. A method as claimed in claim 1 comprising using, as said x-ray detector, an x-ray detector having a narrow detector surface in said longitudinal direction.

5. A method as claimed in claim 1 comprising using, as said x-ray detector, an x-ray detector having an active surface and using only a narrow region of said active detector surface of said x-ray detector for generating each of said partial exposures.

6. A method as claimed in claim 5 comprising using only a middle region of said active surface of said x-ray detector as said narrow region.

7. A method as claimed in claim 1 comprising generating a customized curve set, embodying said curved path for said x-ray source and said x-ray detector, for said examination subject dependent on body parameters of said examination subject.

8. A method as claimed in claim 7 comprising generating said curved path in said curve set by:

classifying said body parameters of said examination subject as representing an examination subject type from among a plurality of examination subject types;

providing a standardized curved path; and scaling said standardized curved path dependent on said examination subject type for producing said curved path in said curve set for said examination subject.

9. A method as claimed in claim 7 comprising generating said curved path in said curve set by:

providing a plurality of standardized curve sets respectively for a plurality of examination subjects having different body parameters; and selecting a curve set for said examination subject from among said plurality of curve sets for which said body parameters most closely match the body parameters of said examination subject.

10. A method as claimed in claim 1 wherein said curved geometry is formed by a spinal column of the examination subject, and comprising moving said x-ray source and said x-ray detector along said curved path corresponding to said spinal column.

11. A method as claimed in claim 10 comprising determining external body dimensions of said examination subject and, from said external body dimensions, determining a length of said spinal column, and using said length of said spinal column to determine said curved path for moving said x-ray source and said x-ray detector.

12. A method as claimed in claim 11 comprising obtaining a reference exposure of said examination subject, before moving said x-ray source and said x-ray detector along said curved path, with said examination subject lying substantially parallel to said longitudinal direction and substantially perpendicular to said projection direction, and obtaining said external body dimensions from said reference x-ray exposure.

13. An x-ray system for producing an x-ray exposure of an examination subject having a longitudinal extent in a longitudinal direction and exhibiting a curved geometry throughout said longitudinal extent, in a projection direction perpendicular to said longitudinal direction, comprising:
- an x-ray source and an x-ray detector adapted to be disposed on opposite sides, respectively, of said examination subject;
- a control device;
- a mounting arrangement, operated by said control device, to which said x-ray source and said x-ray detector are attached; and
- said control device operating said mounting arrangement for moving said x-ray source and said x-ray detector in said longitudinal direction along a curved path substantially co-extensive with said longitudinal extent and substantially conforming to said curved geometry, for producing a plurality of partial exposures, in said projection direction, respectively at a plurality of positions along said curved path; and
- an image computer, supplied with said plurality of partial exposures, for generating an overall exposure of said curved geometry of said examination subject from said partial exposures.

14. An x-ray system as claimed in claim 13 wherein said image computer directly combines said plurally of partial exposures to form said overall image.

15. An x-ray system as claimed in claim 13 wherein said image computer archives said plurally of partial exposures with respective identifications for subsequent combination to form said overall image.

16. An x-ray system claimed in claim 13 wherein said x-ray source and said x-ray detector are mounted in said mounting arrangement for allowing each of said x-ray source and said x-ray detector to be pivoted around an axis perpendicular to said longitudinal direction and perpendicular to said projection direction.

17. An x-ray system as claimed in claim 13 wherein said mounting arrangement allows movement of at least one of said x-ray source and said x-ray detector in said projection direction.

18. An x-ray system as claimed in claim 13 wherein said control device automatically moves at least one of said x-ray source and said x-ray detector along a freely selectable curve, forming said curved path.

19. An x-ray system as claimed in claim 13 wherein said control device controls said mounting arrangement to position said x-ray source and said x-ray detector, at each of said positions along said curved path, to align said x-ray source and x-ray detector and a portion of said examination subject to be imaged in the partial exposure at that position, for causing a partial exposure projection direction for the partial exposure to be acquired at that position to be substantially at a right angle to said portion.

20. An x-ray system as claimed in claim 13 wherein said x-ray detector has an active detector surface that is narrow in said longitudinal direction.

21. An x-ray system as claimed in claim 13 wherein said x-ray detector has a detector surface, and comprising an x-ray detector control device connected to said x-ray detector for activating only a narrow region of said detector surface in said longitudinal direction for generating said plurality of partial exposures.

22. An x-ray system as claimed in claim 13 wherein said control device comprises a memory containing a curve set, including said curved path, customized for said examination subject.

23. An x-ray system as claimed in claim 13 wherein said control device comprises a memory containing a plurality of curve sets, each including a different curved path, respectively for a plurality of different examination subject types, and wherein said control device selects one of said curve sets from said memory, for an examination subject type most closely corresponding to said examination subject, for operating said mounting arrangement for moving said x-ray source and said x-ray detector along the curved path in the selected curve set for producing said plurality of partial exposures.

24. An x-ray system as claimed in claim 13 wherein said control device comprises a memory containing a standardized curve set, and wherein said control device is supplied with data representing a physical measurement of said examination subject and scales said standardized curve set dependent on said data to generate said curved path for moving said x-ray source and said x-ray detector for producing said plurality of partial exposures.

25. An x-ray system as claimed in claim 24 wherein said control device operates said mounting arrangement and said x-ray source and said x-ray detector for generating a reference x-ray exposure of said examination subject lying substantially parallel to said longitudinal direction and substantially perpendicular to said projection direction, before operating said mounting arrangement for moving said x-ray source and said x-ray detector along said curved path, and wherein said control device obtains said data from said reference x-ray exposure.

* * * * *